United States Patent [19]

Roof et al.

[11] 4,036,063
[45] July 19, 1977

[54] SAMPLE DILUTION

[75] Inventors: Lewis B. Roof; Grady T. Porter, both of Bartlesville, Okla.

[73] Assignee: Phillips Petroleum Company, Bartlesville, Okla.

[21] Appl. No.: 719,215

[22] Filed: Aug. 31, 1976

[51] Int. Cl.² .............................................. G01N 1/10
[52] U.S. Cl. ................................ 73/422 GC; 137/604; 259/4 R
[58] Field of Search ........... 73/23, 1, 422 GC, 61.1 C; 259/4 R; 137/604

[56] References Cited

U.S. PATENT DOCUMENTS

| 2,895,496 | 7/1959 | Sanctuary | 137/315 |
|---|---|---|---|
| 3,158,166 | 11/1964 | Warren | 137/835 |
| 3,427,002 | 2/1969 | Wilding | 259/4 R |
| 3,721,253 | 3/1973 | Reincke | 137/3 |

FOREIGN PATENT DOCUMENTS 811,973  5/1969  Canada ................................. 73/1 G

*Primary Examiner*—S. Clement Swisher

[57] ABSTRACT

Two conduit means having a preselected volumetric relationship one to the other, at least one of these conduit means having a plurality of parallel passageways having different flow transmission time characteristics, are utilized in the dilution of a sample by filling one of the conduit means with a diluent liquid and the other with a sample material, then connecting the two conduit means together in a closed conduit loop and circulating the contents of the loop through the loop in order to cause uniform mixing of the sample material with the diluent liquid. In a preferred embodiment the diluted sample material is resampled from the conduit loop for further use or analysis.

16 Claims, 2 Drawing Figures

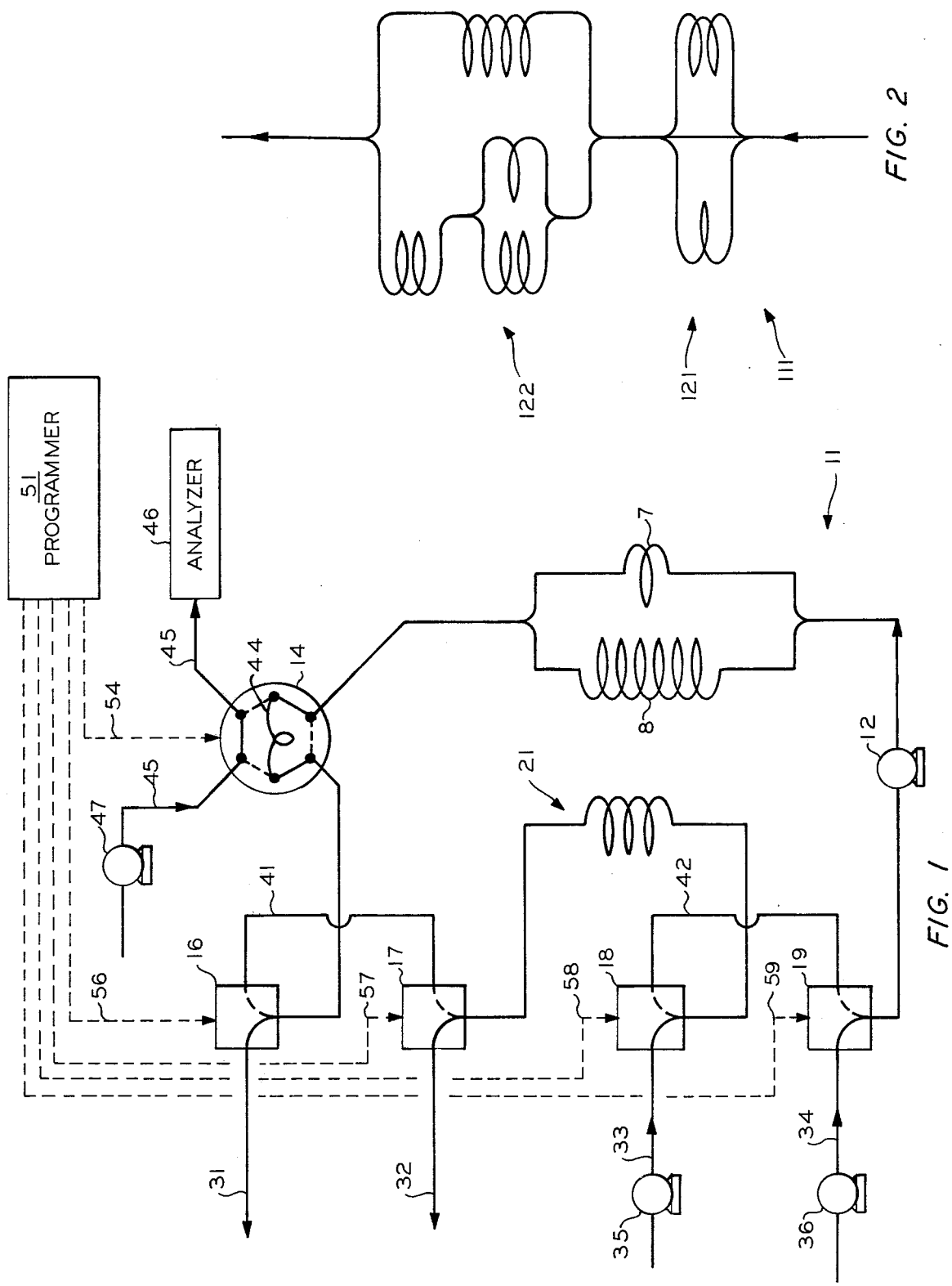

SAMPLE DILUTION

This invention relates to an apparatus and method for diluting a sample. In another aspect the invention relates to an apparatus and method for diluting a sample material using a liquid diluent. In yet another aspect the invention relates to an apparatus and method for automatic dilution of a sample material. In still another aspect the invention relates to an apparatus and method for diluting a sample by continuously circulating preselected volumes of sample material and diluent liquid around a closed conduit loop. In another aspect the invention relates to an improved apparatus for rapidly diluting a sample material.

Samples to be analyzed, particularly those to be analyzed by process liquid chromatography or laboratory liquid chromatography often require dilution prior to analysis. Dilution is ordinarily used to regulate some property of the sample mixture to aid the analysis. For example, the boiling point of the sample can be regulated to prevent solidification or vaporization, the total quantity used for analysis of the sample can be reduced to below that normally available by using a sample injection valve alone, or the viscosity of the sample can be reduced to provide better sample flow through the analysis instrument. In addition to dilution of samples to be analyzed by liquid chromatography, dilution of samples for other purposes is likewise often desirable.

It is particularly desirable to provide an automatic sample dilution system suitable for use with high viscosity samples such as polymers or rubbers which either cannot be analyzed by liquid chromatography in an undiluted state or which require extremely high temperature analyzer operation in order to permit analysis without dilution. In addition, it is desirable to dilute a sample as rapidly as possible to insure the availability of an accurate diluted sample while keeping the sample dilution apparatus and method as simple as possible to provide long-term accuracy and trouble free operation of unattended automatic operation of the dilution system.

Accordingly, an object of the invention is to provide an apparatus and method for diluting a sample. Another object of the invention is to provide an apparatus and method for diluting a sample material using a liquid diluent. Yet another object of the invention is to provide an apparatus and method for automatic dilution of a sample material. Still another object of the invention is to provide an apparatus and method for diluting a sample by continuously circulating preselected volumes of sample material and diluent liquid around a closed circuit loop. Another object of the the invention is to provide an apparatus and method for diluting high viscosity samples. An additional object of the invention is to provide an apparatus and method for rapidly diluting a sample material.

In accordance with the invention an apparatus and method are provided whereby a first conduit means having a first volume is filled with a diluent liquid and a second conduit means having a volume is filled with a diluent liquid and a second conduit means having a volume bearing a predetermined size relationship to the volume of the first conduit means is filled with a sample material. At least one of the first and second conduit means has as a part thereof at least two parallel flow passageways having different flow transmission time characteristics to provide fluid transmission through the parallel passageway combination such that fluid entering one of the passageways will exit that passageway before fluid is transmitted through the remaining one or more parallel passageways. The first and second conduit means are then connected in series to form a closed conduit loop and the contents of the conduit loop are circulated around the loop to cause mixing of the diluent liquid and sample material. The diluted sample material in the conduit loop can then be resampled for analysis or for any other purpose for which a diluted sample is desired. After the desired use is made of the diluted sample material the first and second conduit means can be returned to their initial condition so that diluent liquid can be flushed through the first conduit means and sample material can be flushed through the second conduit means in order to obtain fresh diluent liquid and sample material for use in a subsequent dilution procedure.

Additional objects and advantages of the invention will be apparent from the description thereof and the appended claims thereto, as well as from the detailed description of the drawing in which:

FIG. 1 is a schematic representation of a preferred sample dilution system embodying the apparatus and method of the invention; and FIG. 2 is a schematic representation of an alternative embodiment of a conduit means for use with the apparatus and method of the invention.

Referring to FIG. 1 there is illustrated a first conduit means 11, including parallel flow passageways 7 and 8, a pump means 12, and associated portions of a sample valve means 14, connected at its first end to a first valve means 16 and at its second end to a fourth valve means 19. A second conduit means 21 is connected at its first end to a second valve means 17 and at its second end to a third valve means 18. Each of the valve means 16, 17, 18, and 19 is a two-way valve permitting the establishment of fluid communication between the respective associated conduit end and either of two additional conduit means. Each of the valve means 16, 17, 18, and 19 therefore has a first position schematically illustrated in FIG. 1 by the solid line through the box representing the valve, and a second position schematically illustrated in FIG. 1 by the dashed line through the box representing the respective valve.

When each of the valve means 16, 17, 18, and 19 is in its respective first position as illustrated by FIG. 1, the first valve means 16 establishes fluid communication between the first end of the first conduit means 11 and a diluent disposal conduit 31; the second valve means 17 provides fluid communication between the first end of the second conduit means 21 and a sample disposal conduit 32; the third valve means 18 provides for fluid communication between the second end of the second conduit means 21 and a sample supply conduit 33; and the fourth valve means 19 provides for fluid communication between the second end of the first conduit 11 and a diluent supply conduit 34. When each of the valve means 16, 17, 18, and 19 is in its illustrated first position, therefore. diluent liquid flows through the diluent supply conduit 34, through the fourth valve means 19, and into the second end of the first conduit means 11. The diluent liquid then proceeds through the conduit means 11 through the second end thereof, into the first valve means 16, and from the first valve means 16 into the diluent disposal conduit 31. At the same time, sample material flows through the sample supply conduit 33 and the third valve means 18 into the second end of the second conduit means 21, through the second conduit means 21 to the first end thereof, and then continues through the second valve means 17 into the sample disposal conduit 32. While the sample supply conduit 33 and diluent supply 34 can be provided with appropriate pump means 35 and 36 respectively in order to insure a flow of sample material and diluent liquid to the third valve means 18 and fourth valve means 19 respectively, such pump means 35 and 36 or equivalent means for initiating flow through their respective supply conduits may be necessary in applications where sufficient process or reservoir pressure is available to insure supply conduit flow. In addition, the pump means 12 located in the first conduit means 11 can be used under appropriate conditions to provide flow through the diluent supply conduit 34 and fourth valve means 19 into the first conduit means 11.

After a period of time sufficeint for the flow of diluent material through the first conduit means 11 and sample material through the second conduit means 21 to displace and flush any material remaining from a previous dilution in either of the conduits through the associated disposal conduits 31 and 32 and for the first conduit means 11 and second conduit means 21 to be filled with fresh diluent liquid and sample material respectively, the valve means 16, 17, 18, and 19 are substantially simultaneously switched to their respective second positions. With the valves in their respective second position the first valve means 16 provides fluid communication between the first end of the first conduit means 11 and the first end of a first connecting conduit 41; the second valve means 17 provides fluid communication between the first end of the second conduit means 21 and the second end of the first connecting conduit 41; the third valve means 18 provides fluid communication between the second end of the second conduit means 21 and the first end of a second connecting conduit 42; and the third valve means 19 provides fluid communication between the second end of the first conduit means 11 and the second end of the second connecting conduit 42. In this configuration the first end of the first conduit means 11 and the first end of the second conduit means 21 are connected through the first connecting conduit 41, and the second end of the first conduit means 11 and the second end of the second conduit means 21 are connected through the second connecting conduit 42 to provide a closed loop containing the diluent liquid of the first conduit means 11 and the sample material of the second conduit means 21. Continued actuation of the pump means 12 to provide continuing circuitous circulation of the contents of the closed loop is then used to mix the contents of the closed loop unitl a uniformly diluted sample material mixture is obtained. Circulation through the closed loop can be maintained for as long as necessary to provide a uniformly diluted sample material mixture therein, with the exact time required for each specific apparatus configuration being dependent upon the relative volume of the loop, the speed and capacity of the pump means 12, the solubility and mobility of the sample material in the diluent liquid, the turbulence of flow through the conduit loop, and other similar parameters.

Although continued circulation around a conduit loop not containing a plurality of parallel flow paths such as passageways 7 and 8 can be used to dilute a sample, the use of suitable parallel passageways in accordance with the invention substantially reduces the length of time required to obtain uniform mixing of the sample material and diluent liquid. The flow characteristics of the passageways 7 and 8 are such that one of the passageways, passageway 7 in the illustrated preferred embodiment, for example, delivers fluid flowing therethrough from the upstream confluence of passageways 7 and 8 to the downstream confluence thereof in a length of time less than the time required for passageway 8 to deliver fluid between the same two points. Although such flow characteristics are preferably established by choosing passageways 7 and 8 of different lengths, the same or suitably similar conditions can be provided by choosing passageways 7 and 8 having different resistance to flow resulting from different passageway cross sections or other suitable differing physical parameters. Use of a single pair of parallel flow passageways as illustrated by FIG. 1 in accordance with the invention has permitted dilution of sample material in one third the time required for the same dilution when parallel flow paths were not provided.

The volumes of the first connecting conduit 41 and second connecting conduit 42 are preferably so much smaller than the volume of either the first conduit means 11 or second conduit means 21 that the minute amount of diluted sample material remaining therein from the immediately preceding dilution procedure has an insignificant or negligible effect on the composition of any subsequent diluted sample. As a practical matter such connecting conduits 41 and 42 will ordinarily be no more than a coupling connecting one valve directly to another or, in any of the numerous equivalent apparatus configurations available, a short internal passageway in a double or multiple valve. However, in some applications such as the monitoring of process streams in which substantial rapid changes in sample material will not occur, the volume of the connecting conduits 41 and 42 can be greater, without causing any significant alteration of subsequent sample composition, than they can under similar circumstances in a process where it is important to immediately recognize small and rapidly changing variations in sample material content.

After a period of time sufficient for thorough mixing of the sample material and diluent liquid in the closed conduit loop, the sample valve 14 may be used to inject a preselected volume of sample material from the sample loop 44 thereof into the flow of chromatographic carrier liquid through an analyzer input conduit 45 to a chromatographic analysis means 46. The analyzer input conduit 45 and analysis apparatus 46 can be any suitable liquid chromatographic analysis apparatus or, in the case of a sample which is eluted to provide increased volatility, could be a suitable gas chromatographic analysis apparatus in which the diluted sample material is vaporized to present a gaseous sample to the analysis means 46 for analysis. Although a pump means 47 is illustrated providing chromatographic carrier fluid flow, any suitable means for establishing such flow can be used.

In order to provide for automatic unattended dilution and sampling of successive portions of sample material, a suitable programming means 51 is provided to generate valve actuating signals 54, 56, 57, 58, and 59 to actuate respective valve means 14, 16, 17, 18, and 19 in a preselected timed relationship. As previously indicated, valve means 16, 17, 18, and 19 are preferably simultaneously changed from their illustrated first position (solid lines) to their second position (dashed lines) in order to connect the first conduit means 11 and second conduit means 21 in a series relationship. While the sample valve means 14 is schematically illustrated in a first position (solid lines) wherein the sample loop 44 is included in the first conduit means 11, the size and characteristics of the sample loop 44 may be such that it is desirable to avoid passage of sample material therethrough until it has been completely diluted, and the sample valve means 14 may be maintained in its second position (dotted lines) until after sample material dilution has been accomplished.

When the complete dilution of the sample material has been accomplished and a uniform diluted sample material mixture is contained within the closed conduit loop, the sample valve means 14 is switched to its illustrated first position, if not already in that position, to permit the sample loop 44 to fill with the diluted sample material. After a period of time sufficient for the sample loop 44 to be flushed and filled with diluted sample material, the sample valve means 14 is placed in a second position to inject the sample contained within the sample loop 44 into the flow of material through the carrier conduit 45. After injection of the sample into the analysis system or other use of the diluted sample has been completed, all valves are returned to their initial position for initiation of a subsequent dilution cycle.

Although, as previously indicated, improved mixing times can be achieved using a single pair of parallel passageways 7 and 8 illustrated by FIG. 1, any number of parallel passageways of the use of more than one set of parallel passageways in a particular dilution system can be advantageously used to further shorten the dilution time required for a sample. For example, FIG. 2 is a schematic illustration of a portion of a conduit means 111 employing two sets of parallel passageways, the first set 121 comprising three passageways, each of a different length, in parallel, and the second set 122 comprising one parallel passageway combination within another combination of parallel passageways. There are many additional passageway arrangements which can be advantageously used in the practice of the invention. While the more complex arrangements of parallel passageways will ordinarily tend to provide faster mixing of the sample material and diluent, many complex arrangements may require unnecessarily large volumes of materials and may be more difficult to throughly flush in preparation for a succeeding sample dilution. The presently preferred parallel passageway arrangements are therefore those which are no more complex than necessary to provide the desired mixing within the required or desired length of time. In many cases, knowing the flow characteristics of the particular diluent and sample material involved and knowing the pressures and flow rates which will be induced by the circulating pump means 12, the relative lengths of the parallel passageways used can be advantageously selected by those skilled in the art to further improve the mixing efficiency of the system.

While the specific apparatus embodiment of the invention best suited for each particular application can vary widely, it has been found that for use with standard chromatographic analysis equipment the first and second conduit means 11 and 21 can advantageously be constructed from conduit having an inside diameter of at least about 0.2 inch (standard ¼-inch outside diameter tubing) when use of the system to dilute and lower the viscosity of a particularly viscous sample is desired. Likewise, it is preferred that the paths of fluid communication associated with the pumps and valves incorporated into the apparatus of the invention be large enough to permit the desired circulation of sample material and diluent liquid around the conduit loop to be maintained. Presently preferred apparatus for use in implementing the preferred embodiment of the invention illustrated by FIG. 1 for diluting a viscous rubber or polymer sample in one-third the time required for similar method and apparauts not utilizing parallel flow paths is as follows:

| | |
|---|---|
| Passageway 7 | 2 inch length of 1/4 inch Outside Diameter stainless steel tubing |
| Passageway 8 | 6 inch length of 1/4 inch Outside Diameter stainless steel tubing |
| Remainder of first conduit means 11 | 1/4 inch O.D. 9 feet 4 inches long stainless steel tubing |
| Second conduit means 21 | 1/4 in. O.D. 3 in. long stainless steel |
| Pump means 12, 35 and 36 | Gear pump model 17-51-303 Extraction Sampling Pump, mfg. by Micropump, 1035 Shary Court Concord, Calif. 94518 |
| Sample valve means 14 | High pressure model VIII mfg. by Applied Automation, Inc. Pawhuska Rd., Bartlesville, OK 74004 |
| Valve means 16,17,18, and 19 | Hoke valve No. 7663G4Y mfg. by Hoke Incorporated, Cresskill, N.J. |
| Conduit means 31,32,33, and 34 | Same size or larger than associated conduit means 11 and 21 |
| Pump means 47 | Model MCP-36 mfg. by Haskel Engineering and Supply Co., 100 E. Graham Place Burbank, Calif. 91502 |
| Connecting conduits 41, 42 | 1/4 in. O.D. (2–3 in.) stainless steel or short as possible |
| Carrier fluid supply conduit 45 | 1/6 in. O.D. stainless steel tube |
| Analyzer means 46 | Optichrom L/C liquid chromatographic analyzers sold by Applied Automation, Inc. |
| Programming means 51 | Model 102 sold by Applied Automation, Inc. |

Although the apparatus and method of the invention have described herein in conjunction with a presently preferred embodiment thereof, it is to be understood that reasonable variations and modifications by those skilled in the art of sampling and analysis of various materials are within the scope of the foregoing description of the invention and of the appended claims thereto.

What is claimed is:

1. Apparatus comprising:

first conduit means having a passageway therethrough with a first internal volume;

second conduit means having a passageway therethrough with a second internal volume, said second internal volume having a predetermined size relationship to said first internal volume;

parallel flow passageway means forming at least a portion of at least one of said first and second conduit means for providing at least two parallel passageways having different flow transmission time characteristics through at least a portion of the associated conduit means;

means for filling said passageway of said first conduit means with a diluent liquid;

means for filling said passageway of said second conduit means with a sample material;

means for connecting said passageway of said first conduit means and said paassageway of said second conduit means to form a closed conduit loop; and means for circulating said diluent liquid and sample material through said conduit loop to cause mixing thereof.

2. Apparatus in accordance with claim 1 additionally comprising means for removing a preselected volume of diluted sample material from said conduit loop.

3. Apparatus in accordance with claim 1 wherein said means for circulating comprises a pump means.

4. Apparatus in accordance with claim 3 wherein said pump means is associated with said first conduit means.

5. Apparatus in accordance with claim 1 wherein said first and second conduit means comprise tubing having an inside diameter greater than about 0.2 inches.

6. Apparatus in accordance with claim 1 wherein both said first and second conduit means comprise tubing having substantially the same inside diameter.

7. Apparatus in accordance with claim 2 additionally comprising means for analyzing said preselected volume of diluted sample material removed from said conduit loop.

8. Apparatus in accordance with claim 1 herein said first conduit means has first and second ends and said second ends and said second conduit means has first and second ends and wherein said means for filling said first conduit means, said means for filling said second conduit means and said means for connecting said first conduit means and said second conduit means comprise:

first valve means associated with said first end of said first conduit means and having a first position for establishing fluid communication between said first conduit means and a diluent disposal conduit and a second position for establishing fluid communication between said first conduit means and the first end of a first connecting conduit;

second valve means associated with said first end of said second conduit means and having a first position for establishing fluid communication between said second conduit means and a sample disposal conduit and a second position for establishing fluid communication between said second conduit means and the second end of said first connecting conduit;

third valve means associated with said second end of said second conduit means and having a first position for establishing fluid communication between said second conduit means and a sample supply conduit and a second position for establishing fluid communication between said second conduit means and the first end of a second connecting conduit;

fourth valve means associated with said second end of said first conduit means and having a first position for establishing fluid communication between said first conduit means and a diluent supply conduit and a second position for establishing fluid communication between said first conduit and the second end of said second connecting conduit; and programming means for automatically placing said first, second, third and fourth valve means in their respective first positions to fill said first conduit means with said diluent liquid and to fill said second conduit means with said sample material, and for automatically placing said first, second, third and fourth valve means in their respective second positions to connect said first and second conduit means through said first and second connecting conduits to form said conduit loop.

9. Apparatus in accordance with claim 1 wherein said parallel flow passageway means forms a part of said first conduit means.

10. Apparatus in accordance with claim 1 wherein said at least two parallel passageways comprise passageways having different lengths.

11. Apparatus in accordance with claim 1 wherein said at least two parallel passageways comprise passageways having different resistance to liquid flow.

12. A method for diluting a sample, said method comprising:

introducing a first preselected volume of a sample material into a first portion of a circuitous path;

introducing a second preselected volume of a diluent liquid into a second portion of said circuitous path;

circulating said sample material and diluent liquid around said circuitous path;

dividing the flow around said circuitous path at a first point on said circuitous path into a plurality of flows having different flow transmission time characteristics; and combining said plurality of flows into a single flow at a second point on said circuitous path.

13. A method in accordance with claim 12 additionally comprising continuing circulating said sample material and diluent liquid until a desired degree dilution is achieved.

14. A method in accordance with claim 12 wherein circulating said diluent liquid and sample material comprises continuously pumping the contents of said circuitous path in a preselected direction around said path.

15. A method in accordance with claim 14 wherein said sample material comprises a polymeric material.

16. A method in accordance with claim 14 wherein said sample material comprises a rubber material.

* * * * *

UNITED STATES PATENT AND TRADEMARK OFFICE
CERTIFICATE OF CORRECTION

PATENT NO. : 4,036,063

DATED : July 19, 1977

INVENTOR(S) : Lewis B. Roof et al

It is certified that error appears in the above-identified patent and that said Letters Patent are hereby corrected as shown below:

Column 7, claim 8, line 42, after "claim 1", delete "herein" and substitute therefor --- wherein ---.

Column 7, claim 8, line 44, delete "second ends and said" as it is a duplication.

Signed and Sealed this

Twenty-sixth Day of June 1979

[SEAL]

Attest:

RUTH C. MASON
Attesting Officer

DONALD W. BANNER
Commissioner of Patents and Trademarks